United States Patent
Shan

(10) Patent No.: US 12,426,877 B2
(45) Date of Patent: Sep. 30, 2025

(54) CARTRIDGE ASSEMBLY AND SURGICAL STAPLER

(71) Applicant: Touchstone International Medical Science Co., Ltd., Suzhou (CN)

(72) Inventor: Teng Shan, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 0 days.

(21) Appl. No.: 18/687,579

(22) PCT Filed: Aug. 31, 2022

(86) PCT No.: PCT/CN2022/116033
§ 371 (c)(1),
(2) Date: Feb. 28, 2024

(87) PCT Pub. No.: WO2023/030356
PCT Pub. Date: Mar. 9, 2023

(65) Prior Publication Data
US 2024/0382194 A1   Nov. 21, 2024

(30) Foreign Application Priority Data
Aug. 31, 2021   (CN) .......................... 202111015426.0

(51) Int. Cl.
*A61B 17/064* (2006.01)
*A61B 17/072* (2006.01)

(52) U.S. Cl.
CPC .............................. *A61B 17/0644* (2013.01); *A61B 2017/07271* (2013.01)

(58) Field of Classification Search
None
See application file for complete search history.

(56) References Cited

U.S. PATENT DOCUMENTS 9,788,835 B2 * 10/2017 Morgan ........... A61B 17/07207
2010/0213241 A1   8/2010 Bedi
(Continued)

FOREIGN PATENT DOCUMENTS

| CN | 210811269 U | 6/2020 |
| CN | 111528948 A | 8/2020 |

(Continued)

OTHER PUBLICATIONS

International Search report issued in PCT/CN2022/116033 on Dec. 6, 2022.

*Primary Examiner* — Nathaniel C Chukwurah
(74) *Attorney, Agent, or Firm* — Fox Rothschild LLP

(57) ABSTRACT

A cartridge assembly and a surgical stapler are provided. The cartridge assembly includes: a staple strip including a staple strip body; a support member; a cartridge cover including a second surface arranged relative to the first surface of the staple strip body, wherein a first gap is formed between the first surface of the staple strip body and the second surface of the cartridge cover; a firing member including a cutting portion, wherein the highest point of the cutting portion is higher than the first surface of the staple strip body. By forming the first gap, the cutting portion of the firing member is higher than the first surface of the staple strip, which facilitates the cutting portion to separate the staples from the staple strip body.

19 Claims, 17 Drawing Sheets

(56) References Cited

U.S. PATENT DOCUMENTS

2014/0263557 A1* 9/2014 Schaller ........... A61B 17/07207
                                                227/176.1
2020/0046356 A1  2/2020 Baxter, III et al.

FOREIGN PATENT DOCUMENTS

| CN | 111789645 A | 10/2020 |
| CN | 112006739 A | 12/2020 |
| CN | 213821558 U | 7/2021 |
| CN | 215874787 U | 2/2022 |
| WO | 2018176414 A1 | 10/2018 |

* cited by examiner

CARTRIDGE ASSEMBLY AND SURGICAL STAPLER

CROSS-REFERENCE TO RELATED APPLICATIONS

This application is based upon PCT patent application No. PCT/CN2022/116033, filed on Aug. 31, 2022, which claims priority to Chinese Patent Application No. 202111015426.0, filed on Aug. 31, 2021, the entire contents of which are incorporated herein by reference.

TECHNICAL FIELD

The present disclosure relates to surgical instruments' technology, more particularly, to a cartridge assembly and a surgical stapler.

BACKGROUND

In the prior art, the surgical stapler generally includes an instrument platform, a firing handle rotatably connected to the instrument platform, and a head assembly installed on the instrument platform. The head assembly can pass through a small incision in the body by a trocar, thus approaching the surgical site and performing the surgery. The head assembly includes a cartridge assembly and an anvil arranged relatively. The cartridge assembly includes a staple strip, a support member that supports the staple strip, and a cartridge cover that accommodates the staple strip and the support member, a firing member is arranged on the proximal side of the cartridge cover. When the stapler is fired, the cutter is moved toward the distal side by pushing the cutter pushing rod, and the cutter drives the firing member to move toward the distal side of the stapler. The firing member pushes the staple that is rotatably connected to the staple strip body out, and the cutting portion of the firing member separates the staples from the staple strip body. The cutter cuts the tissue between the cartridge assembly and the anvil to fire the stapler.

In the existing surgical stapler, the inner surface of the cartridge cover abuts the upper surface of the staple strip. The upper surface of the cutting portion located at the top of the firing member may be lower than or at the same height as the upper surface of the staple strip. When the firing member moves to the distal side, the cutting portion cannot separate the staples from the staple strip body easily, which may result in the staple being unable to be separated from the staple strip body.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site. In the stapler, the inner side and the outer side are used herein with reference to the axis of the stapler. The side close to the axis is the inner side, and the side far from the axis is the outer side.

SUMMARY

To solve the problems in the prior art, the present disclosure provides a cartridge assembly and a surgical stapler, by forming a first gap between the first surface of the staple strip body and the second surface of the cartridge cover, the cutting portion of the firing member is higher than the first surface of the staple strip, which facilitates the cutting portion to separate the staples from the staple strip body.

In the present disclosure, a cartridge assembly including: a staple strip including a staple strip body extending along an axial direction; a support member, wherein the staple strip body is installed on one side of the support member, and the staple strip body includes a first surface away from the support member; a cartridge cover at least partially covering the first surface of the staple strip body, wherein the cartridge cover includes a second surface arranged relative to the first surface of the staple strip body, and a first gap is formed between the first surface of the staple strip body and the second surface of the cartridge cover; a firing member, movably disposed at the bottom of the cartridge cover, and movable in the axial direction, wherein the firing member includes a cutting portion, and the highest point of the cutting portion is higher than the first surface of the staple strip body in a height direction.

The present disclosure further provides a surgical stapler including the above cartridge assembly.

The cartridge assembly and the surgical stapler have the following advantages.

The present disclosure provides a cartridge assembly and a surgical stapler, by forming a first gap between the first surface of the staple strip body and the second surface of the cartridge cover, the cutting portion of the firing member is higher than the first surface of the staple strip, which facilitates the cutting portion to separate the staples from the staple strip body. Thus, it can ensure that when the stapler is fired, the firing member can push the staples out toward the anvil and then the staples are closed on the tissue.

BRIEF DESCRIPTION OF THE DRAWINGS

By reading the detailed description of non-limiting embodiments with reference to the following drawings, other features, objectives, and advantages of the present disclosure will become more apparent.

DETAILED DESCRIPTION

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

The present disclosure provides a cartridge assembly and a surgical stapler including the cartridge assembly. The surgical stapler includes an instrument platform, a firing handle rotatably connected to the instrument platform, and a head assembly installed on the instrument platform. The head assembly includes a cartridge assembly and an anvil arranged relatively. The cartridge assembly includes: a staple strip including a staple strip body extending along an axial direction of the stapler, a support member, wherein the staple strip body is installed on one side of the support member, and the staple strip body includes a first surface away from the support member; a cartridge cover at least partially covering the first surface of the staple strip body, the cartridge cover includes a second surface arranged relative to the first surface of the staple strip body, and a first gap is formed between the first surface of the staple strip body and the second surface of the cartridge cover; a firing member, movably disposed at the bottom of the cartridge cover, and movable in the axial direction, wherein the firing member includes a cutting portion, and the highest point of the cutting portion is higher than the first surface of the staple strip body in a height direction; wherein the cutting portion is used to separate the staples from the staple strip body when the stapler is fired.

The present disclosure provides a cartridge assembly and a surgical stapler, by forming a first gap between the first surface of the staple strip body and the second surface of the cartridge cover, the cutting portion of the firing member is higher than the first surface of the staple strip, which facilitates the cutting portion to separate the staple from the staple strip. Thus, it can ensure that when the stapler is fired, the firing member can push the staples out toward the anvil and then the staples are closed on the tissue.

In the following, the structures of the cartridge assembly in specific embodiments are described by combining FIGS. 1-17. It should be understood that the specific embodiments are not intended to be a limitation to the protection scope of the present disclosure.

Figure 1:
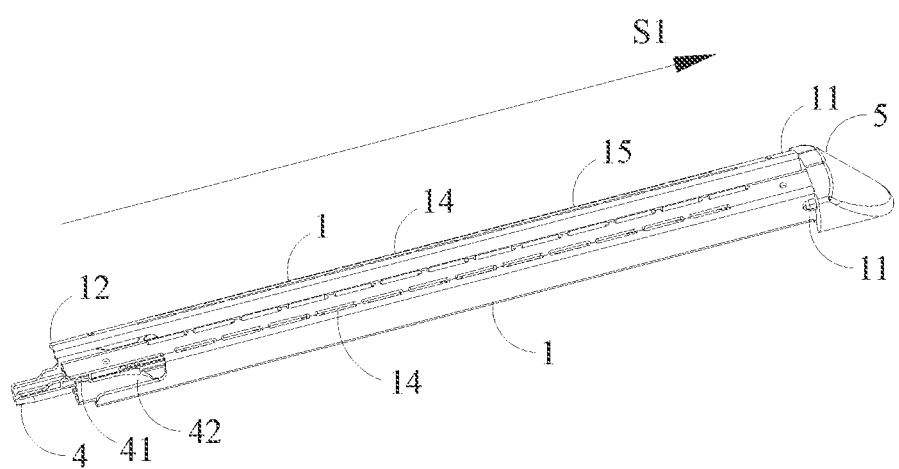
FIG. 1 is a structural schematic view of a cartridge assembly according to a first embodiment of the present disclosure.
Figure 2:
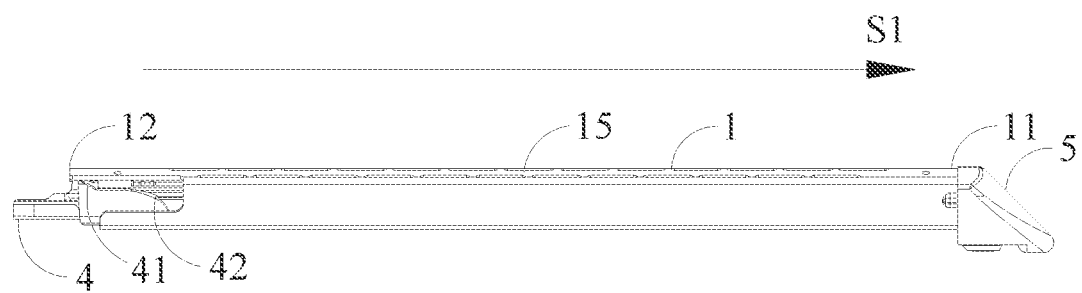
FIG. 2 is a front view of a cartridge assembly according to the first embodiment of the present disclosure.
Figure 3:
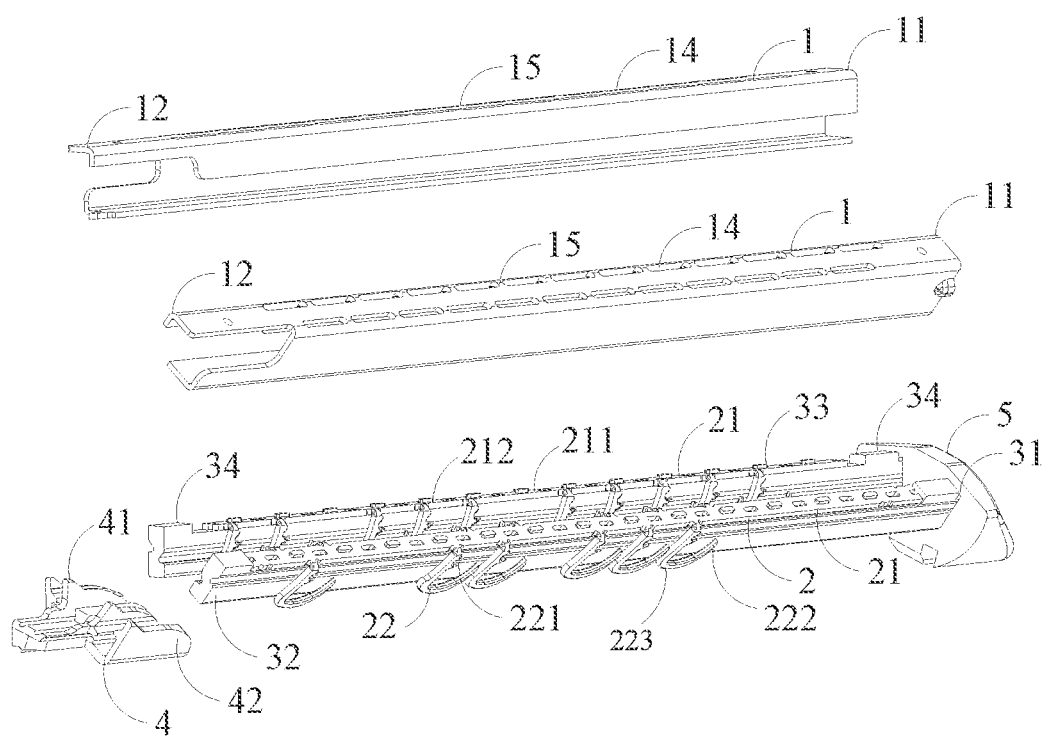
FIG. 3 is an exploded schematic view of a cartridge assembly according to the first embodiment of the present disclosure.

FIGS. 1-8 illustrate the structure of the cartridge assembly in the first embodiment of the present disclosure. As shown in FIGS. 1-3, the cartridge assembly includes a staple strip 2, a support member 3 for supporting the staple strip 2, a cartridge cover 1 for accommodating the support member 3 and the staple strip 2, and a firing member 4 at least partially entering the cartridge cover 1. The staple strip 2 includes a staple strip body 21 extending along the axial direction and a plurality of staples 22 connected to the staple strip body 21. The staples 22 are rotatably connected to the staple strip body 21 via connecting portions 221. The cartridge assembly further includes a fixing member 5, wherein the distal side 31 of the support member 3 and the distal side 11 of the cartridge cover 1 are both fixed to the fixing member 5. In this embodiment, two support assemblies 3, two staple strips 2, and two cartridge covers 1 are provided. Each of the two staple strips 2 is respectively set on the corresponding support member 3, and the staples 22 are arranged on both sides of each staple strip 2. The cartridge cover 1 is jacketed on the support assemblies 3 and the staple strips 2. In alternative embodiments, the number of the support member 3, the staple strip 2, and the cartridge cover 1 can be varied as needed, and are not limited to that shown in the figures. Additionally, the staples 22 may also be present on only one side of the staple strip 2. All of these variations are within the scope of the present disclosure. In FIG. 3, only a partial representation of the staples 22 is shown for illustrative purposes. In actual applications, the number and arrangement of the staples 22 can be selected as needed.

Figure 4:
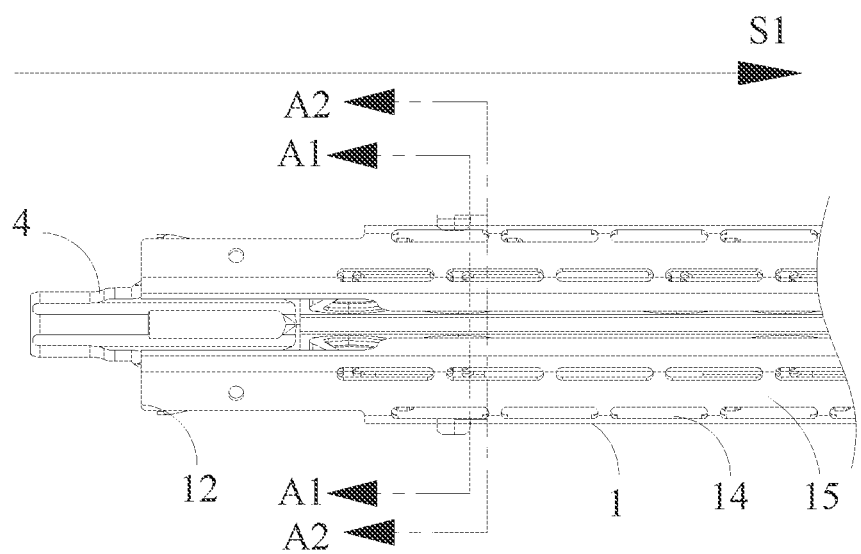
FIG. 4 is a top view of a cartridge assembly according to the first embodiment of the present disclosure.
Figure 5:
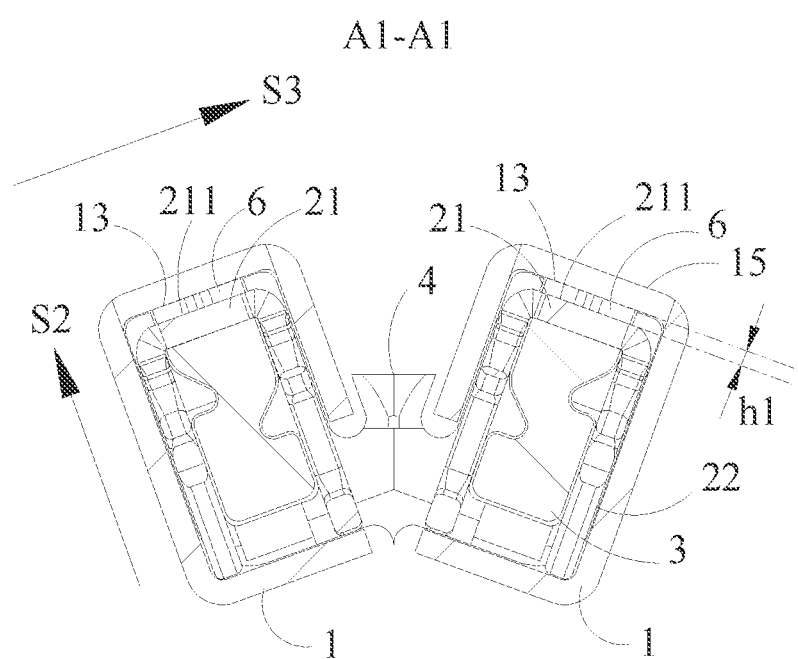
FIG. 5 is a sectional view in the direction A1-A1 of FIG. 4.

The staple strip body 21 is mounted on one side of the support member 3. In the perspective shown in FIG. 3 and FIG. 5, the staple strip body 21 is positioned on the upper side of the support member 3. The staple strip body 21 includes a first surface 211 away from the support member 3, that is, an upper surface of the staple strip body 21 is the first surface 211. As shown in FIGS. 3-5, the cartridge cover 1 at least partially covers the first surface 211 of the staple strip body 21. The cartridge cover 1 includes a second surface 13 arranged relative to the first surface 211 of the staple strip body 21. The second surface 13 of the cartridge cover 1 refers to a surface of the cartridge cover 1 that is arranged relative to the staple strip body 21. In this embodiment, the second surface 13 of the cartridge cover 1 is an inner surface of an upper plate of the cartridge cover 1. The cartridge cover 1 further includes a fourth surface 15 configured to be located on the outer side of the second surface 13, which corresponds to an outer surface of the upper plate of the cartridge cover 1. The cartridge cover 1 is provided with staple holes 14 through the upper plate.

Figure 15:
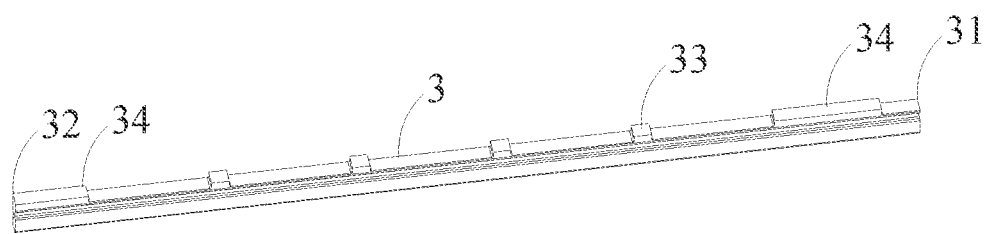
FIG. 15 is a structural schematic view of a support member according to the fourth embodiment of the present disclosure.
Figure 16:
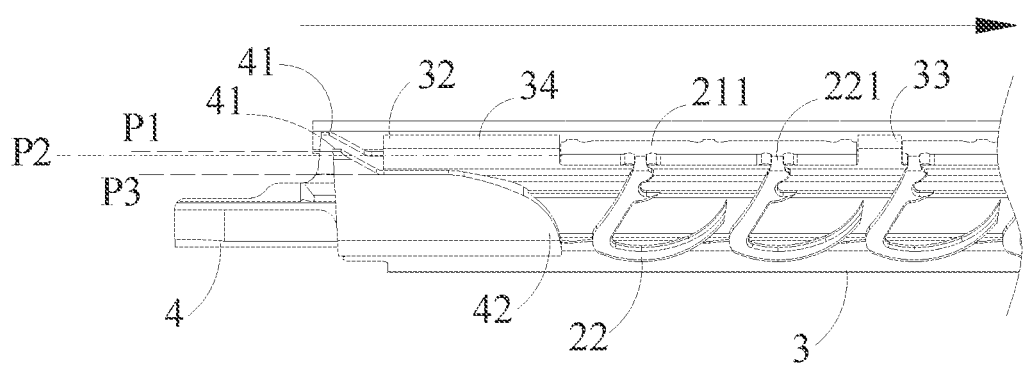
FIG. 16 is a structural schematic view of a part of a cartridge assembly omitting the cartridge cover according to a fourth embodiment of the present disclosure.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site. The direction along the axis of the stapler is the axial direction, that is, the direction from the distal side to the proximal side of the stapler, or from the proximal side to the distal side. For example, in the perspective of FIG. 1, for the cartridge cover 1, its distal side 11 is on the right side, and the proximal side 12 is on the left side. In the perspective of FIG. 15, for the support member 3, its distal side 31 is on the right side, and the proximal side 32 is on the left side.

Figure 6:
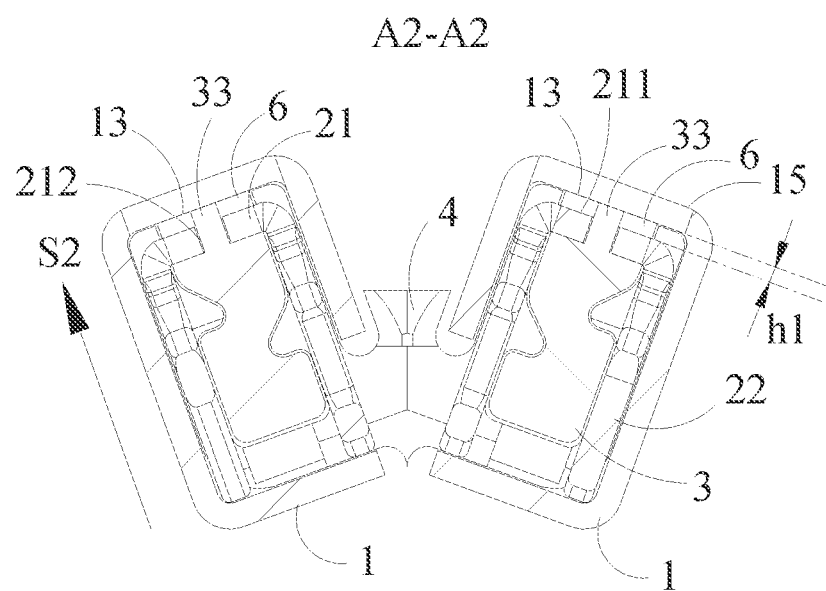
FIG. 6 is a sectional view in the direction A2-A2 of FIG. 4.
Figure 7:
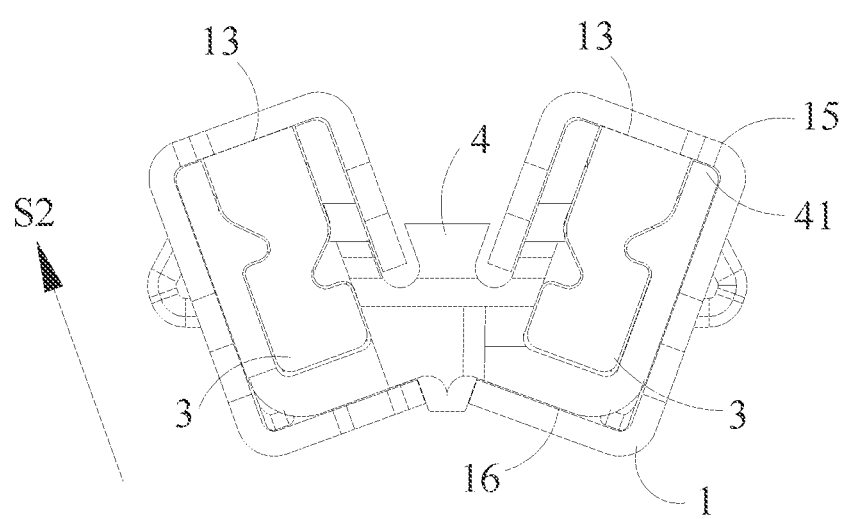
FIG. 7 is a left view of a cartridge assembly according to the first embodiment of the present disclosure.

In the present disclosure, the S1 direction refers to the direction from the proximal side to the distal side of the surgical stapler. The S1 direction or the direction opposite to the S1 direction is defined as the axial direction of the stapler. The S2 direction shown in FIGS. 5-7 is defined as a longitudinal direction, i.e., the height direction. The S3 direction perpendicular to the S1 direction and the S2 direction is defined as a lateral direction, i.e., the width direction. In the present disclosure, for a component, the inner and outer sides are relative to the axis of the stapler, where the side close to the axis is the inner side, and the side far from the axis is the outer side.

Figure 8:
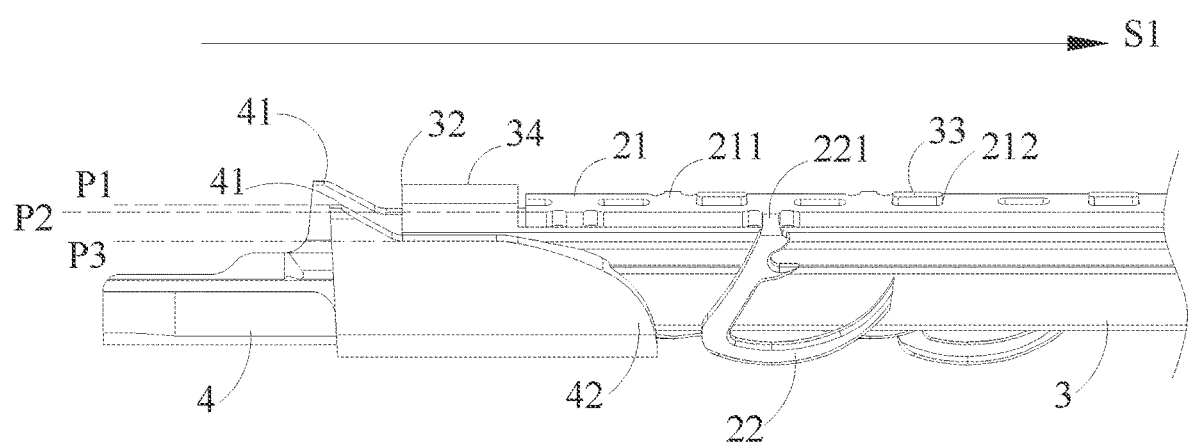
FIG. 8 is a structural schematic view of a part of a cartridge assembly omitting the cartridge cover according to the first embodiment of the present disclosure.
Figure 9:
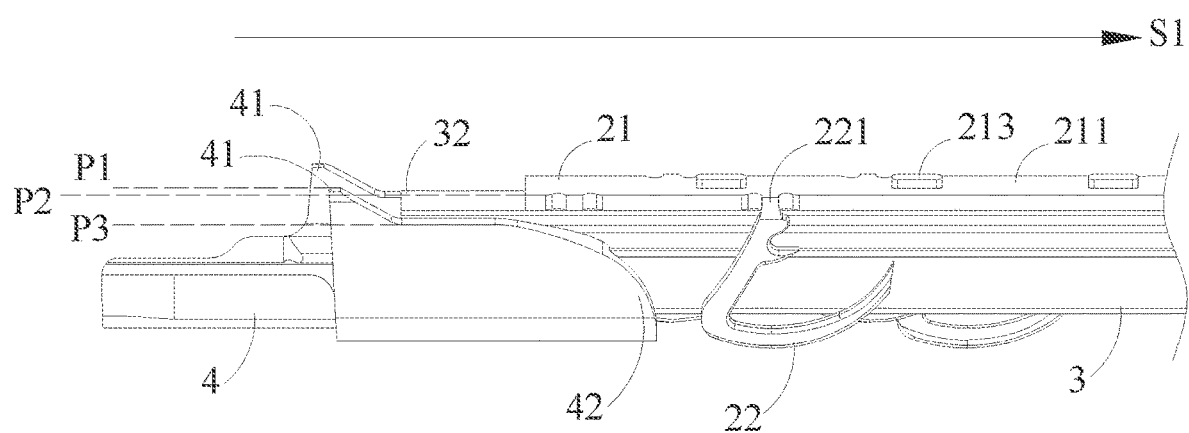
FIG. 9 is a structural schematic view of a part of a cartridge assembly omitting the cartridge cover according to a second embodiment of the present disclosure.

As shown in FIGS. 3-5, a first gap 6 is formed between the first surface 211 of the staple strip body 21 and the second surface 13 of the cartridge cover 1. The height from an upper surface to a bottom surface of the first gap 6 is h1. The height h1 of the first gap 6 can be adjusted to different values as the size of the cartridge assembly changes. The firing member 4 is initially positioned on the proximal side 12 of the cartridge cover 1 and is movable along the axial direction. As shown in FIG. 7 and FIG. 8, the firing member 4 includes a cutting portion 41 and a pushing portion 42, where the pushing portion 42 is located at the distal side of the cutting portion 41. During the process of firing the stapler, the pushing portion 42 first contacts the staples 22, the staples are rotated and closed, so that the legs of the staples 22 to extend outward from the cartridge cover 1. Subsequently, the cutting portion 41 contacts the connecting portion 221 and cuts, so that the connecting portion 221 are separated from the staple strip body 21, thereby the staples 22 are separated from the staple strip body 21. The staples 22 can be fully ejected from the cartridge cover 1 through the staple holes 14 and then stapled onto the tissue. As shown in FIG. 8, P1 is a line indicating the position of the highest point of the cutting portion 41 in the height direction. P2 is a line indicating the position of the first surface 211 of the staple strip body 21 in the height direction. P1 is higher than P2, so that the cutting portion 41 of the firing member 4 can easily separate the staples 22 from the staple strip body 21, and during the process of firing the stapler, the firing member 4 can push the staples 22 out and toward the anvil and staple them onto the tissue.

As shown in FIG. 7, in the embodiment, the highest point of the cutting portion 41 of the firing member 4 respectively abuts the second surface 13 of the cartridge cover 1, so that the cutting portion 41 of the firing member 4 can maximize the use of the first gap 6, the cutting portion 41 can easily separate the staples 22 from the staple strip 2. The cartridge cover 1 further includes a third surface 16 arranged relative to the second surface 13, and a lower surface of the firing member 4 respectively abuts the third surface 16 of the cartridge cover 1. In the embodiment, the third surface 16 of the cartridge cover 1 is an upper surface of a bottom plate of the cartridge cover 1. By utilizing the third surface 16 and the second surface 13 of the cartridge cover 1, the firing member 4 keeps stable in the vertical direction. As the firing member 4 moves along the axial direction within the cartridge cover 1, the highest point of the cutting portion 41 of the firing member 4 remains consistently higher than the first surface 211 of the staple strip body 21 in the height direction, so that all staples 22 can be completely separated from the staple strip body 21.

In the embodiment, as shown in FIG. 8, P3 is a line indicating the position of the lowest point of the cutting portion 41 of the firing member 4 in the height position, and P3 is lower than P2. P1 is a line indicating the position of the highest point of the cutting portion 41 in the height direction. P1 is higher than the connecting portion 221 in the height direction. Therefore, at least part of the cutting portion 41 of the firing member 4 is aligned with the connecting portion 221 in the axial direction, so that the staples 22 are completely separated from the staple strip body 21 and stapled onto the tissue when the surgical stapler is being fired.

As shown in FIGS. 3-8, in the embodiment, a surface of the support member 3 includes at least one first convex portion 33. One side surface of the first convex portion 33 away from the support member 3 (i.e., an upper surface of the first convex portion 33), is higher than the first surface 211 of the staple strip body 21 in the height direction. The upper surface of the first convex portion 33 respectively abuts the second surface 13 of the cartridge cover 1, forming the first gap 6 between the first surface 211 of the staple strip body 21 and the second surface 13 of the cartridge cover 1 through the supporting action of the first convex portion 33. The first convex portion 33 includes a first portion located between the second surface 13 of the cartridge cover 1 and the first surface 211 of the staple strip body 21, and a second portion located between the first surface 211 of the staple strip body 21 and the upper surface of the support member 3. A height from an upper surface to a bottom surface of the first portion of the first convex portion 33 is equal to that of the portion of the first convex portion 33 protruding from the first surface 211 of the staple strip body 21, and this height is equal to the height h1 of the first gap 6.

As shown in FIG. 3 and FIG. 6, in the embodiment, a surface of the first convex portion 33, located away from the staple strip body 21, is affixed in parallel with the second surface 13 of the cartridge cover 1, thereby enhancing the cooperative stability between the first convex portion 33 and the staple strip body 21. As shown in FIG. 3 and FIG. 8, a lateral distance between inner and outer surfaces of the first convex portion 33 is less than that of the staple strip body 21, meaning that the lateral width of the first convex portion 33 is smaller than the lateral width of the staple strip body 21. The surface of the staple strip body 21 is provided with at least one mounting hole 212, through which the first convex portion 33 is inserted. Preferably, the first convex portion 33 is fixedly attached to the mounting hole 212 through welding.

As shown in FIG. 8, in the embodiment, the first convex portion 33 is a boss, and a projection of the boss on the first surface 211 of the staple strip body 21 is a rounded rectangle, meaning that each corner of the boss is provided with rounded guide surfaces, which can better guide the boss into the mounting hole 212 during the assembly of the staple strip 2 and the support member 3. The shape of the first convex portion 33 provided here is for illustrative purposes only. In other alternative embodiments, the first convex portion 33 can also have different shapes, for example the projection of the first convex portion 33 on the first surface 211 of the staple strip body 21 is a rectangle, triangle, diamond, trapezoid, etc., on the first surface 211 of the staple strip body 21, and the area of the upper surface of the first convex portion 33 can be different from that of the lower surface of the first convex portion 33, for example, the first convex portion 33 may have a pyramidal structure with a larger lower surface area and a smaller upper surface area, all of which fall within the scope of the present disclosure. The number of the first convex portions 33 and mounting holes 212 can be set to correspond one-to-one, or there can be more mounting holes 212 than the first convex portions 33.

In the embodiment, the surface of the support member 3 is also provided with two second convex portions 34, located respectively at the proximal and distal sides of the support member 3. A surface of each second convex portion 34 away from the support member 3 (i.e., an upper surface of the second convex portion 34) is higher than the first surface 211 of the staple strip body 21 in the height direction, and the upper surface of each second convex portion 34 respectively abuts the second surface 13 of the cartridge cover 1. The upper surface of the first convex portion 33 is at the same height as that of the upper surface of the second convex portion 34. In the embodiment, a lateral distance between inner and outer surfaces of each second convex portion 34 is equal to that of the staple strip body 21. Preferably, each second convex portion 34 can be fixedly attached to the staple strip body 21 through welding.

In the embodiment, the number and arrangement of the first convex portions 33 can be selected according to requirements and can be evenly or unevenly distributed along the axial direction on the surface of the support member 3; In another alternative embodiment, the surface of the support member 3 can only have the first convex portions 33 without the second convex portions 34; In another alternative embodiment, the surface of the support member 3 can only have the second convex portions 34 without the first convex portions 33. In another alternative embodiment, the second convex portions 34 can be only set on the distal side or only on the proximal side. In another alternative embodiment, the second convex portions 34 can also have the same shape and size as the first convex portions 33.

Figure 10:
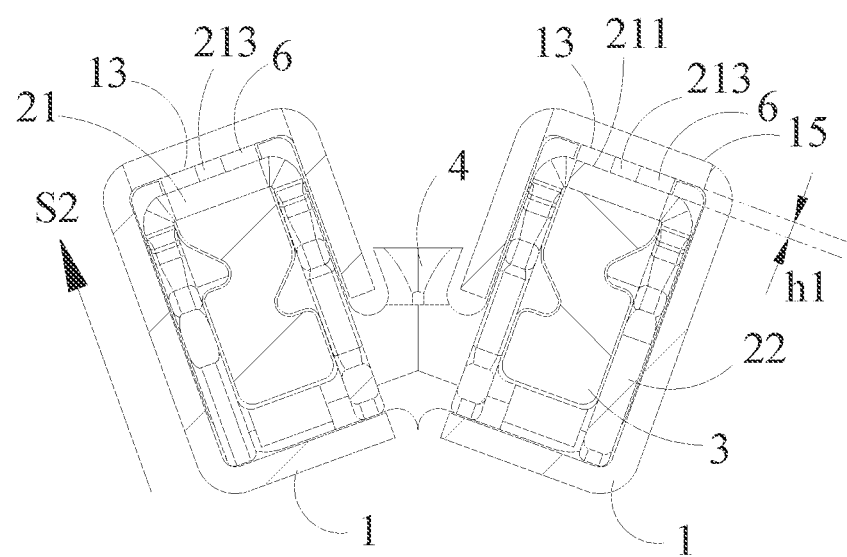
FIG. 10 is a schematic view showing a staple strip cooperating with a cartridge cover according to the second embodiment of the present disclosure.

The structure of the cartridge assembly in the second embodiment of the present disclosure is illustrated in FIG. 3 and FIG. 10. The difference between the embodiment and the first embodiment is that the surface of the support member 3 does not have the first convex portion 33 and the second convex portion 34. Instead, the first surface 211 of the staple strip body 21 is provided with at least one third convex portion 213. The surface away from the staple strip body 21 of the third convex portion 213 (i.e., an upper surface of the third convex portion 213) respectively abuts the second surface 13 of the staple cartridge cover 1, thereby forming the first gap 6 between the first surface 211 of the strip body 21 and the second surface 13 of the cartridge cover 1. The height from an upper surface to a bottom surface of the third convex portion 213 is equal to the height h1 of the first gap 6. The upper surface of the third convex portion 213 is affixed in parallel with the second surface 13 of the cartridge cover 1, thereby enhancing the cooperative stability. The shape, size, number, and arrangement of the third convex portion 213 can be selected as needed, and are not limited to those shown in the figures. The embodiment also achieves the purpose of conveniently driving the cutting portion 41 of the firing member 4 to separate the staples 22 from the staple strip body 21.

Figure 11:
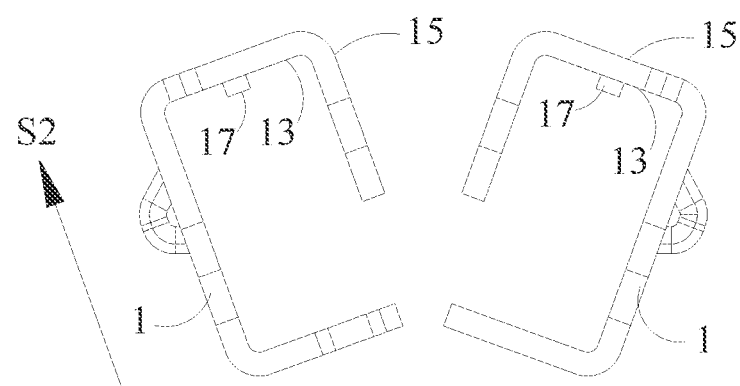
FIG. 11 is a structural schematic view of a cartridge cover according to a third embodiment of the present disclosure.
Figure 12:
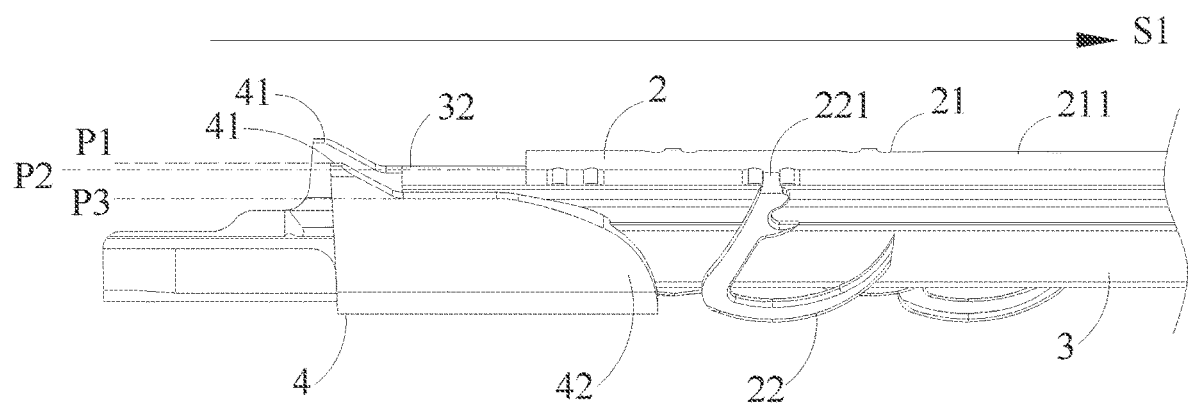
FIG. 12 is a structural schematic view of a part of a cartridge assembly omitting the cartridge cover according to the third embodiment of the present disclosure.

FIG. 11 and FIG. 12 illustrate the structure of the cartridge assembly in the third embodiment of the present disclosure. The difference between the embodiment and the first embodiment is that the surface of the support member 3 does not have the first convex portion 33 and the second convex portion 34. Instead, the second surface 13 of the cartridge cover 1 is provided with a fourth convex portion 17 protruding towards the staple strip 2. A surface away from the staple strip body 21 of the fourth convex portion 17 (i.e., a lower surface of the fourth convex portion 17), respectively abuts the first surface 211 of the staple strip body 21. A height from an upper surface to a bottom surface of the fourth convex portion 17 is equal to the height h1 of the first gap 6. The lower surface of the fourth convex portion 17 is affixed in parallel with the first surface 211 of the staple strip body 21, thereby enhancing the cooperative stability. The shape, size, number, and arrangement of the fourth convex portion 17 can be selected as needed, and are not limited to those shown in the figures. The embodiment also achieves the purpose of conveniently driving the cutting portion 41 of the firing member 4 to separate the staples 22 from the staple strip body 21.

In the first, second, and third embodiments described above, the convex portions are respectively arranged on the support member 3, the staple strip body 21, and the cartridge cover 1 to form the first gap 6 between the first surface 211 of the staple strip body 21 and the second surface 13 of the cartridge cover 1. In other alternative embodiments, these three embodiments can be combined. For example, simultaneously setting two or more of the first convex portion 33, the second convex portion 34, the third convex portion 213, and the fourth convex portion 17 falls within the scope of the present disclosure.

FIGS. 13-16 illustrate the structure of the cartridge assembly in the fourth embodiment of the present disclosure. The fourth embodiment is similar to the first embodiment, with the first convex portion 33 and two second convex portions 34 being arranged on the surface of the support member 3. The two second convex portions 34 are configured to be located on the distal side 31 and proximal side 32 of the support member 3, with the first convex portion 33 positioned between them, and the upper surfaces of the first convex portion 33 and the second convex portion 34 respectively abutting against the second surface 13 of the cartridge cover 1. The difference between the fourth embodiment and the first embodiment is that: in the fourth embodiment, the cartridge assembly includes multiple staple strips 2 arranged along the axial direction, and the first convex portion 33 is positioned between adjacent staple strip bodies 21 of the two staple strips 2. The two second convex portions 34 are respectively configured to be located on the distal side of the furthest staple strip 2 and the proximal side of the nearest staple strip 2. In the embodiment, the first convex portion 33 and/or the second convex portion 34 are preferably fixedly connected to the staple strip body 21. For example, the first convex portion 33 and the second convex portion 34 are fixedly connected to the staple strip body 21 by welding or other means.

Figure 13:
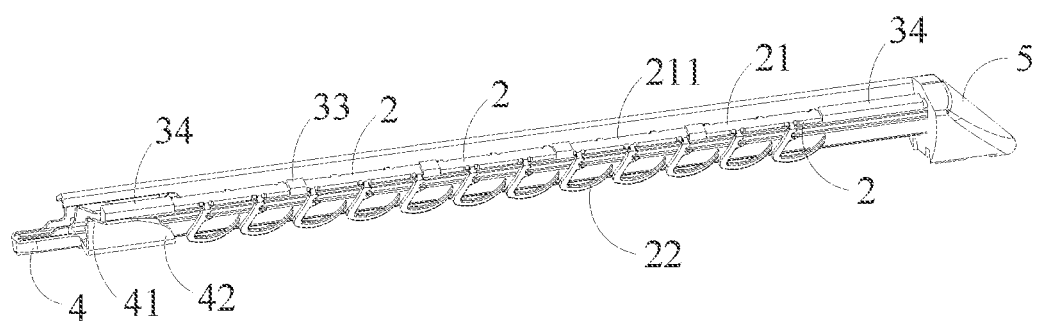
FIG. 13 is a structural schematic view of a cartridge assembly omitting the cartridge cover according to a fourth embodiment of the present disclosure.
Figure 14:
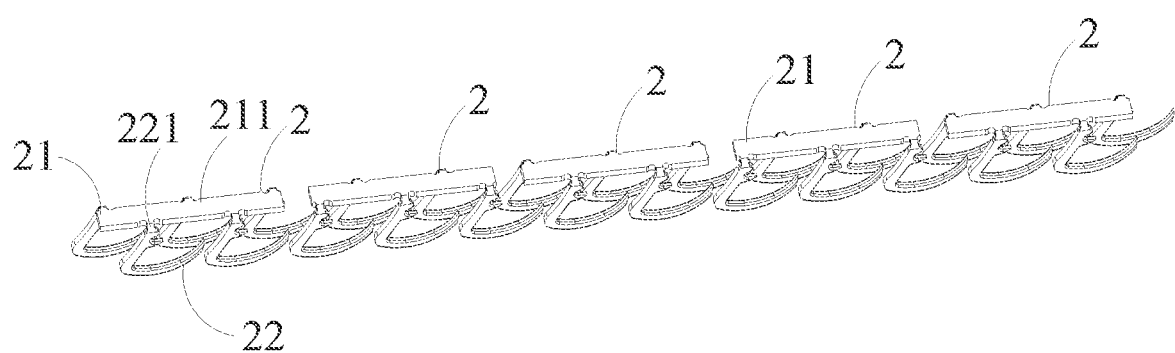
FIG. 14 is a structural schematic view of a staple strip according to the fourth embodiment of the present disclosure.

As shown in FIGS. 13-15, In this embodiment, a lateral distance between inner and outer surfaces of the first convex portion 33 is equal to that of the staple strip body 21, i.e., a lateral width of the first convex portion 33 is equal to a lateral width of the staple strip body 21, facilitating better positioning of multiple staple strips 2 during installation and enhancing the stability of the staple strips 2. In other alternative embodiments, the lateral distance between the inner and outer surfaces of the first convex portion 33 can also be less than that of the staple strip body 21. For example, using the shape and size of the first convex portion 33 as in the first embodiment is also within the scope of the present disclosure.

This fourth embodiment can also have many variations, all of which fall within the scope of the present disclosure. The number, size, shape, and arrangement of the first convex portion 33 and the second convex portion 34 in the fourth embodiment are not limited to those shown in the drawings. The length of the staple strip 2 along the axial direction and the number of staple strip 2 are also not limited to those shown in the figures and can be adjusted as needed. In an alternative embodiment, only the first convex portion 33 can be provided and no second convex portion 34 is provided.

Figure 17:
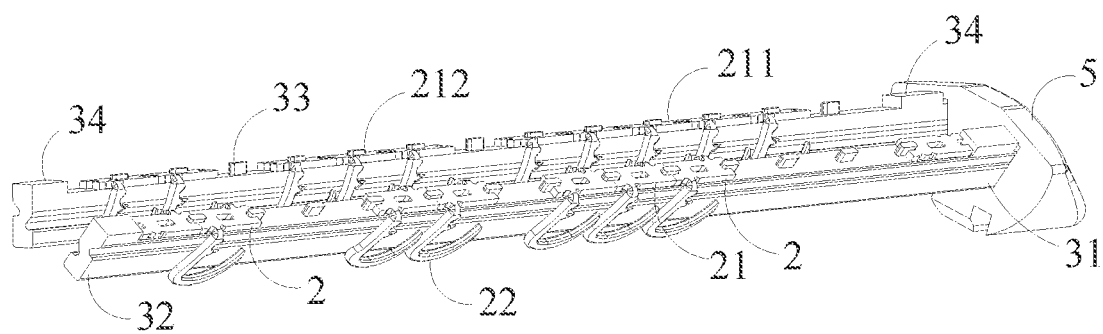
FIG. 17 is a schematic view showing a staple strip cooperating with a support member according to a fifth embodiment of the present disclosure.

FIG. 17 illustrates the structure of the cartridge assembly in the fifth embodiment of the present disclosure. The difference between the embodiment and the fourth embodiment is that the configuration of the first convex portion 33 is different. Similarly, multiple staple strips 2 are arranged along the axial direction on the support member 3 in the fifth embodiment. The shape and configuration of the first convex portion 33 in the fifth embodiment are similar to those in the first embodiment, that is, the lateral distance between the inner and outer surfaces of the first convex portion 33 is less than that of the staple strip body 21. The surface of the staple strip body 21 is provided with at least one mounting hole 212, through which the first convex portion 33 is inserted. The mounting hole 212 can be provided in two ways. One way is that the mounting hole 212 is fully located in a staple strip body 21 of a staple strip 2. The other way is that each of the adjacent staple strip bodies 21 of two staple strips 2 can be provided with a half-hole. After the two staple strip bodies 21 are assembled along the axial direction, the two half-holes combine to form a mounting hole 212.

The fifth embodiment can also have many variations, all of which fall within the scope of the present disclosure. The number, size, shape, and arrangement of the first convex portion 33 and the second convex portion 34 in the fifth embodiment are not limited to those shown in the drawings. The length and number of staple strips 2 along the axial direction are not limited to those shown in the drawings and can be adjusted as needed. In an alternative embodiment, only the first convex portion 33 can be provided without the second convex portion 34.

In all the embodiments described above, the staple strips 2 are made of biocompatible materials. In preferred embodiments, the staple strip body 21 and the staples 22 may be made of different materials. For example, in some embodiments, the staple strip body 21 may be made of non-absorbable and non-degradable materials such as titanium, titanium alloys, and stainless steel, while the staples 22 may be preferably made of materials which are both bioabsorbable and biocompatible, or biocompatible materials that are both biodegradable and bioabsorbable. After suturing the staples 22 on the tissue, there is no need for subsequent staple removal operations. For example, the staples 22 may be made of materials such as magnesium, magnesium alloys, and degradable polymer materials, but the present disclosure is not limited thereto. Furthermore, the surface of the staples 22 may be coated with a biocompatible coating that is both degradable and biodegradable. The coating can further enhance the hardness of the staples 22 and adjust their degradation rate. For example, the coating may be made of absorbable materials such as L-PLA (PLLA) and/or DL-PLA (PDLLA), but the present disclosure is not limited thereto. The degradation rate of the staples 22 as a whole can be adjusted by adjusting the thickness of the coating. Alternatively, the coating may be a hemostatic agent, which can improve bleeding during the anastomosis process. In other embodiments, the surface of the staples 22 may have a magnetic coating. When exposed to an external magnetic field, the coating is magnetized, thereby enhancing the staple strength. The external magnetic field may be an electromagnetic field, the magnetic field intensity of which can be adjusted to meet the requirements of the anastomosis process, or the external magnetic field may be a permanent magnetic field.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A cartridge assembly comprising:
   a staple strip comprising a staple strip body extending along an axial direction and multiple staples connected to the staple strip body;
   a support member, wherein the staple strip body is installed on one side of the support member, and the staple strip body comprises a first surface away from the support member;
   a cartridge cover at least partially covering the first surface of the staple strip body, wherein the cartridge cover comprises a second surface arranged relative to the first surface of the staple strip body, and a first gap is formed between the first surface of the staple strip body and the second surface of the cartridge cover;
   a firing member, movably disposed at the bottom of the cartridge cover, and movable in the axial direction, wherein the firing member comprises a cutting portion, the cutting portion is configured to separate the staples from the staple strip body, and the highest point of the cutting portion is higher than the first surface of the staple strip body in a height direction;
   at least one convex portion, wherein the convex portion comprises a first portion located between the first surface of the staple strip body and the second surface of the cartridge cover, and the height from an upper surface to a lower surface of the first portion of the convex portion is equal to that of the first gap;
   at least one convex portion, wherein the convex portion comprises a first portion located between the first surface of the staple strip body and the second surface of the cartridge cover, and the height from an upper surface to a lower surface of the first portion of the convex portion is equal to that of the first gap.

2. The cartridge assembly of claim 1, wherein the highest point of the cutting portion of the firing member abuts the second surface of the cartridge cover.

3. The cartridge assembly of claim 1, wherein the lowest point of the cutting portion of the firing member is lower than the first surface of the staple strip body in the height direction.

4. The cartridge assembly of claim 1, wherein each staple is rotatably connected to the staple strip via a connecting portion, and the highest point of the cutting portion of the firing member is higher than the connecting portion in the height direction.

5. The cartridge assembly of claim 1, wherein the convex portion is configured to be located on either the support member or the staple strip body, and a surface of the convex portion away from the staple strip body abuts the second surface of the cartridge cover.

6. The cartridge assembly of claim 5, wherein the surface of the convex portion away from the staple strip body is affixed in parallel with the second surface of the cartridge cover.

7. The cartridge assembly of claim 1, wherein a surface of the support member is provided with at least one first convex portion, a surface of the first convex portion away from the support member is higher than the first surface of the staple strip body in the height direction, and a surface of the first convex portion away from the support member abuts the second surface of the cartridge cover.

8. The cartridge assembly of claim 7, wherein a lateral distance between an inner side and outer side of the first convex portion is smaller than that of the staple strip body, and wherein a surface of the staple strip body is provided with at least one mounting hole, through which the first convex portion is inserted.

9. The cartridge assembly of claim 8, wherein the first convex portion is a boss, and a projection of the boss on the first surface of the staple strip body is a rounded rectangle.

10. The cartridge assembly of claim 7 comprising multiple staple strips arranged along the axial direction, wherein the first convex portion is positioned between the staple strip bodies of adjacent two staple strips.

11. The cartridge assembly of claim 10, wherein the first convex portion is fixedly connected to the staple strip body.

12. The cartridge assembly of claim 1, wherein a surface of the support member is provided with at least one second convex portion, wherein the second convex portion is configured to be located on a proximal and/or a distal side of the support member, a surface of the second convex portion away from the support member is higher than the first surface of the staple strip body in the height direction, and a surface of the second convex portion away from the support member abuts the second surface of the cartridge cover.

13. The cartridge assembly of claim 12, wherein the second convex portion is fixedly connected to the staple strip body.

14. The cartridge assembly of claim 12, wherein a surface of the support member further comprises at least one first convex portion distributed along the axial direction, and a surface of the first convex portion away from the support member is at the same height as the surface of the second convex portion away from the support member.

15. The cartridge assembly of claim 1, wherein the first surface of the staple strip body is provided with at least one third convex portion, and a surface of the third convex portion away from the support member abuts the second surface of the cartridge cover.

16. The cartridge assembly of claim 1, wherein the second surface of the cartridge cover is provided with a fourth convex portion towards the staple strip, and a surface of the fourth convex portion facing the staple strip body abuts the first surface of the staple strip body.

17. The cartridge assembly of claim 16, wherein a surface of the fourth convex portion facing the staple strip body is affixed in parallel with the first surface of the staple strip body.

18. The cartridge assembly of claim 1, wherein the cartridge cover further comprises a third surface arranged relative to the second surface, and a lower surface of the firing member abuts the third surface of the cartridge cover.

19. A surgical stapler comprising the cartridge assembly according to claim 1.

* * * * *